United States Patent [19]

Evans

[11] Patent Number: 4,741,846

[45] Date of Patent: May 3, 1988

[54] 2,4,6-TRIFUNCTIONALIZED PHENOLS

[75] Inventor: Samuel Evans, Marly, Switzerland

[73] Assignee: CIBA-GEIGY Corporation, Ardsley, N.Y.

[21] Appl. No.: 758,014

[22] Filed: Jul. 24, 1985

[30] Foreign Application Priority Data

Aug. 2, 1984 [CH] Switzerland .................. 3729/84

[51] Int. Cl.$^4$ .......................................... C16M 129/00
[52] U.S. Cl. ..................... 252/47.5; 568/39; 568/44; 568/45; 568/50; 568/51; 568/52; 568/55; 564/162; 560/8; 560/9; 558/396; 558/392; 558/393; 558/396; 558/404; 558/405; 558/406; 558/408; 558/410; 252/482
[58] Field of Search ............... 252/475, 482; 568/51, 568/39, 44, 45, 50, 52, 55; 564/162; 560/8, 9; 558/390, 392, 396, 393, 404, 406, 405, 408, 410

[56] References Cited

U.S. PATENT DOCUMENTS

| | | | |
|---|---|---|---|
| 2,322,376 | 6/1943 | McCleary et al. | 252/48 |
| 3,660,352 | 5/1972 | Song | 260/49.95 |
| 3,903,173 | 9/1975 | Eggensperger et al. | 568/51 |
| 4,091,037 | 5/1978 | Arold | 260/609 |
| 4,521,320 | 6/1985 | Spivack et al. | 252/47.5 |

OTHER PUBLICATIONS

F. A. Abdullaeva et al., Azerb Khim Zh 1973, 66 (=CA, 83, 79881h (1975)).

Primary Examiner—William R. Dixon, Jr.
Assistant Examiner—Cynthia A. Prezlak
Attorney, Agent, or Firm—Luther A. R. Hall

[57] ABSTRACT

Novel compounds of the formula I

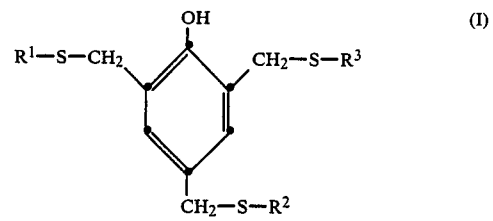

are described. The radicals $R^1$, $R^2$ and $R^3$ are hydroxyl-substituted alkyl, $-C(R^4R^5)-(CHR^6)_m-W$, $-(CH_2)_2-OCOR^{10}$ or

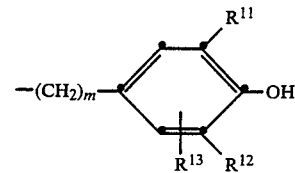

and W is $-COR^7$, $-COOR^7$, $-CON(R^9R^{15})$ or CN. The other radicals are customary hydrocarbon radicals.

The novel substances can be employed as stabilizers for organic polymers or for lubricants.

11 Claims, No Drawings

2,4,6-TRIFUNCTIONALIZED PHENOLS

The present invention relates to novel 2,4,6-trifunctionalized phenols, compositions containing these compounds and their use for stabilising organic materials.

Trifunctionalized phenols containing thiomethyl are known. Thus special compounds of this type are described in Azerb. Khim. Zh., 1973 (5–6), 66–69 as antioxidants for polymers.

Inter alia, phenols containing tris-alkylthiomethyl are described in U.S. Pat. No. 2,417,118 as additives for mineral oils.

The present invention relates to compounds of the formula I

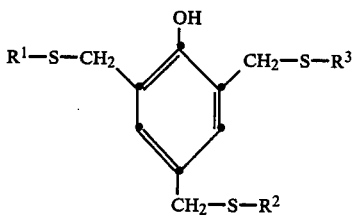

in which $R^1$, $R^2$ and $R^3$ independently of one another are $C_2$–$C_{20}$-alkyl, $-C(R^4R^5)-(CHR^6)_n-W$ or $-(CH_2)_2-OCOR^{10}$ which is substituted by one or two hydroxyl groups or are a radical

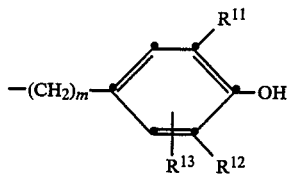

in which $R^4$, $R^5$ and $R^6$ independently of one another are hydrogen, $C_1$–$C_6$-alkyl, phenyl or cyclohexyl, W is $-COR^7$, $-COOR^8$, $-CON(R^{15}R^9)$ or $-CN$, $R^7$ being hydrogen, $C_1$–$C_{20}$-alkyl, $C_5$–$C_{12}$-cycloalkyl, phenyl, 1-naphthyl, 2-naphthyl, $C_7$–$C_{14}$-aralkyl or $C_7$–$C_{14}$-alkaryl, $R^8$ being $C_1$–$C_{20}$-alkyl, $C_5$–$C_{12}$-cycloalkyl, phenyl, 1-naphthyl, 2-naphthyl, $C_7$–$C_{14}$-aralkyl, $C_7$–$C_{14}$-alkaryl or $C_2$–$C_{20}$-alkyl which is substituted by a hydroxyl or cyano group, or $C_2$–$C_{12}$-alkenyl, $C_2$–$C_{12}$-alkinyl or phenyl which is substituted by one or two $-NO_2$, $-Cl$, $-Br$, $-OCH_3$ or $-COOR^{14}$ groups, or a radical

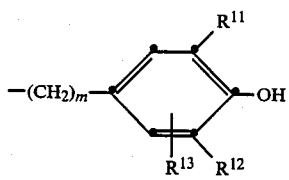

or $C_3$–$C_{20}$-alkyl which is interrupted by one to five $-O-$, $-S-$, $-N(CH_3)-$, $-N(C_2H_5)-$ or $-SO_2-$ groups and is unsubstituted or substituted by a hydroxyl group, it being necessary for any hetero-atoms occurring several times to be separated by at least one methylene group, $R^9$ having one of the meanings of $R^8$ or being additionally hydrogen, $R^{15}$ having one of the meanings of $R^9$, or $R^9$ and $R^{15}$, together with the common nitrogen atom, forming a 5-membered, 6-membered or 7-membered, heterocyclic ring which can if desired also contain a further hetero-atom, $R^{10}$ being $C_1$–$C_{20}$-alkyl, $C_5$–$C_{12}$-cycloalkyl, phenyl, 1-naphthyl, 2-naphthyl, $C_7$–$C_{14}$-aralkyl, $C_7$–$C_{14}$-alkaryl or a radical

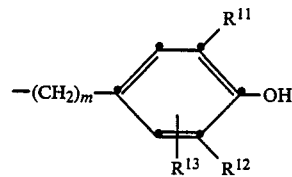

m being 0, 1 or 2, n being 0 or 1, $R^{11}$, $R^{12}$ or $R^{13}$ independently of one another being hydrogen, $C_1$–$C_{20}$-alkyl, cyclohexyl or phenyl and, finally, $R^{14}$ being $C_1$–$C_6$-alkyl, phenyl, cyclohexyl, benzyl or tolyl.

As $C_2$–$C_{20}$-alkyl which is substituted by one or two hydroxyl groups, $R^1$, $R^2$ or $R^3$ are, for example, 2-hydroxyethyl, 2-hydroxypropyl, 2-hydroxybutyl, 2-hydroxyhexyl, 2-hydroxyoctyl, 2-hydroxydecyl, 2-hydroxydodecyl, 2-hydroxytetradecyl, 2-hydroxyhexadecyl, 2-hydroxyoctadecyl, 2-hydroxyeicosyl or 2,3-dihydroxypropyl. 2-Hydroxyethyl, 2-hydroxypropyl or 2,3-dihydroxypropyl is preferred.

As $C_1$–$C_{20}$-alkyl, $R^7$, $R^8$, $R^9$, $R^{10}$, $R^{11}$, $R^{12}$, $R^{13}$ or $R^{15}$ are, for example, methyl, ethyl, n-propyl, isopropyl, n-butyl, sec.-butyl, tert.-butyl, n-pentyl, isopentyl, n-hexyl, 1,1-dimethylbutyl, n-heptyl, n-octyl, 2-ethylhexyl, n-nonyl, n-decyl, 1,1,3,3-tetramethylbutyl, 1,1,3,3-tetramethylhexyl, n-undecyl, n-dodecyl, 1,1,3,3,5,5-hexamethylhexyl, 2,2,4,6,6-pentamethylhept-4-yl, n-tetradecyl, n-hexadecyl, n-octadecyl or n-eicosyl.

$R^7$, $R^8$, $R^9$, $R^{10}$, $R^{11}$, $R^{12}$, $R^{13}$ or $R^{15}$ are preferably $C_1$–$C_{12}$-alkyl and then are, for example, methyl, ethyl, n-propyl, isopropyl, n-butyl, sec.-butyl tert.-butyl, n-pentyl, isoamyl, n-hexyl, n-heptyl, n-octyl, 1,1,3,3-tetramethylbutyl, n-nonyl, n-decyl, n-dodecyl, 2,2,4,6,6-pentamethylhept-4-yl or 1,1,3,3,5,5-hexamethylhexyl.

$R^{11}$, $R^{12}$ or $R^{13}$ are very particularly preferentially branched $C_3$–$C_{12}$-alkyl and, as such, are, for example, isopropyl, sec.-butyl, tert.-butyl, tert.-pentyl, 1,1-dimethylbutyl, 2-ethylhexyl, 1,1,3,3-tetramethylbutyl, 1,1,3,3-tetramethylhexyl, 2,2,4,6,6-pentamethylhept-4-yl or 1,1,3,3,5,5-hexamethylhexyl; but are especially tert.-butyl.

As $C_1$–$C_6$-alkyl, $R^4$, $R^5$, $R^6$ and $R^{14}$ are, for example, methyl, ethyl, n-propyl, isopropyl, n-butyl, sec.-butyl, tert.-butyl, n-pentyl, isopentyl or n-hexyl. Linear $C_1$–$C_6$-alkyl radicals are particularly preferred, and methyl is very particularly preferred.

As $C_5$–$C_{12}$-cycloalkyl, $R^7$, $R^8$, $R^9$, $R^{10}$ or $R^{15}$ are, for example, cyclopentyl, cyclohexyl, cycloheptyl, cyclooctyl, cyclononyl, cyclodecyl, cycloundecyl or cyclododecyl. $C_5$–$C_9$-cycloalkyl is preferred and cyclohexyl is very particularly preferred.

As $C_2$–$C_{12}$-alkenyl, $R^8$, $R^9$ and $R^{15}$ are, for example, vinyl, allyl, but-3-enyl, pent-4-enyl, hex-5-enyl, oct-7-enyl, dec-9-enyl or dodec-11-enyl. Vinyl or allyl is preferred. As $C_2$–$C_{12}$-alkinyl, $R^8$ and $R^9$ are, for example, ethinyl, propargyl, but-3-inyl, hex-5-inyl, oct-7-inyl, dec-9-inyl or dodec-11-inyl. Propargyl is preferred.

As $C_7$–$C_{14}$-aralkyl, $R^7$, $R^8$, $R^9$, $R^{10}$ or $R^{15}$ are, for example, benzyl, phenylethyl, α-methylbenzyl, α,α-dimethylbenzyl, phenylbutyl, phenyl-α,α-dimethylpropyl, phenylhexyl, phenyl-α,α-dimethylbutyl, phenyloctyl or phenyl-α,α-dimethylhexyl. Benzyl is preferred.

As $C_7$–$C_{14}$-alkaryl, $R^7$, $R^8$, $R^9$, $R^{10}$ or $R^{15}$ are, for example, o-, m- or p-tolyl, 2,3-, 2,4-, 2,5-, 2,6-, 3,4-, 3,6-dimethylphenyl, o-, m- or p-ethylphenyl, o-, m- or p-propylphenyl, o-, m- or p-isopropylphenyl, o-, m- or p-butylphenyl, o-, m- or p-sec.-butylphenyl, o-, m- or p-tert.-butylphenyl, 2,3-, 2,4-, 2,5-, 2,6-, 3,4-, 3,5- or 3,6-dibutylphenyl or 2,3-, 2,4-, 2,5-, 2,6-, 3,4-, 3,5- or 3,6-di-tert.-butylphenyl or o-, m- or p-hexylphenyl or o-, m- or p-octylphenyl. o-, m- or p-tolyl is preferred.

As $C_2$–$C_{20}$-alkyl which is substituted by a hydroxyl or cyano group, $R^8$, $R^9$ or $R^{15}$ are, for example, 2-hydroxyethyl, 2-hydroxypropyl, 2-hydroxybutyl, 2-hydroxyhexyl, 2-hydroxyoctyl, 2-hydroxydecyl, 2-hydroxydodecyl, 2-hydroxytetradecyl, 2-hydroxyhexadecyl, 2-hydroxyoctadecyl, 2-hydroxyeicosyl or 2-cyanoethyl. 2-Hydroxyethyl, 2-hydroxypropyl or 2-cyanoethyl is preferred.

As $C_3$–$C_{20}$-alkyl which is interrupted by one to five —O—, —S—, —N(CH$_3$)—, —N(C$_2$H$_5$)— or —SO$_2$— groups, and is unsubstituted or substituted by a hydroxyl group, $R^8$, $R^9$ or $R^{15}$ are, for example, 3-oxabutyl, 3,6-dioxaheptyl, 3,6,9-trioxadecyl, 3,6,9,12-tetraoxatridecyl, 3,6,9,12,15-pentaoxyhexadecyl, 3,6,9,12,15,18-hexaoxanonadecyl, 5-hydroxy-3-oxapentyl, 8-hydroxy-3,6-dioxaoctyl, 11-hydroxy-3,6,9-trioxaundecyl, 14-hydroxy-3,6,9,12-tetraoxatetradecyl, 3-thiabutyl, 5-hydroxy-3-azamethylpentyl, 5-hydroxy-3-azaethylpentyl, 3-azamethyl-6-oxaheptyl, 3-azaethyl-6-oxaheptyl, 3-azamethylbutyl or 3-azaethylbutyl. $C_3$–$C_{12}$-alkyl radicals which are interrupted by —O— and are unsubstituted or substituted by a hydroxyl group are preferred. 5-Hydroxy-3-oxapentyl or 3-oxabutyl is very particularly preferred.

As phenyl which is substituted by one or two —NO$_2$—, —Cl, —Br, —OCH$_3$ or —COOR$^{14}$ groups, $R^8$, $R^9$ or $R^{15}$ are, for example, o-, m- or p-nitrophenyl, o-, m- or p-chlorophenyl, o-, m- or p-bromophenyl, o-, m- or p-methoxyphenyl, o-, m- or p-methoxycarbonylphenyl, o-, m- or p-ethoxycarbonylphenyl, 2,3-, 2,4-, 2,5-, 2,6-, 3,4- or 3,5-dinitrophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 2,3-, 2,4-, 2,5-, 2,6-, 3,4- or 3,5-dimethoxycarbonylphenyl or 2,3-, 2,4-, 2,5-, 2,6-, 3,4- or 3,5-diethoxycarbonylphenyl. o-, m- or p-chlorophenyl, o-, m- or p-methoxyphenyl or o-, m- or p-methoxycarbonylphenyl is preferred.

If $R^9$ and $R^{15}$, together with the common nitrogen atom, form a 5-membered, 6-membered or 7-membered, heterocyclic ring which can, if desired, also contain a further hetero-atom, this ring is, for example, pyrrole, 2-H-pyrrole, imidazole, pyrazole, pyrrolidine, pyrroline, imidazolidine, imidazoline, pyrazolidine, pyrazoline, piperidine, piperazine, hexamethyleneimine or morpholine. Pyrrole, pyrolidine, hexamethyleneimine, piperidine or morpholine is preferred and piperidine or morpholine is very particularly preferred.

Compounds of the formula I which are particularly preferred are those in which $R^1$, $R^2$ and $R^3$ independently of one another are 2-hydroxyethyl, 2-hydroxypropyl or 2,3-dihydroxypropyl.

Compounds of the formula I which are also of interest are those in which $R^1$, $R^2$ and $R^3$ independently of one another are —C(R$^4$R$^5$)—(CHR$^6$)$_n$—W, —(CH$_2$)$_2$—OCOR$^{10}$ or a radical

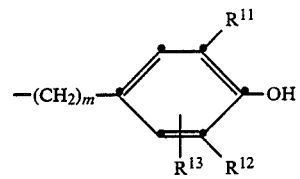

the radicals W, $R^4$, $R^5$, $R^6$, $R^{10}$, $R^{11}$, $R^{12}$ and $R^{13}$ and the indices m and n being as defined above.

Compounds of the formula I which are particularly preferred are those in which $R^1$, $R^2$ and $R^3$ independently of one another are —C(R$^4$R$^5$)—(CHR$^6$)$_n$—W, —(CH$_2$)$_2$—OCOR$^{10}$ or a radical

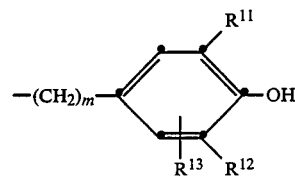

in which $R^4$, $R^5$ and $R^6$ independently of one another are hydrogen or methyl, W is —COR$^7$, —COOR$^8$, —CON(R$^9$R$^{15}$) or —CN in which R$^7$ is $C_1$–$C_{12}$-alkyl, $C_5$–$C_9$-cycloalkyl, phenyl, benzyl or tolyl, $R^8$, $R^9$ and $R^{15}$ have the same meaning as $R^7$ or are additionally 2-hydroxyethyl, 2-hydroxypropyl or 2-cyanoethyl, allyl, propargyl or phenyl which is substituted by a —Cl, —COOCH$_3$ or —OCH$_3$ group, or are a radical

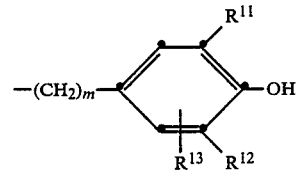

or in which $R^8$, $R^9$ and $R^{15}$ are $C_3$–$C_{12}$-alkyl which is interrupted by one to five —O— groups and is unsubstituted or substituted by a hydroxyl group, it being necessary for an oxygen atoms occurring several times to be separated by at least one methylene group, or in which $R^9$ and $R^{15}$, together with the common nitrogen atom, form a pyrrole, pyrrolidine, piperidine or morpholine ring, $R^{10}$ is $C_1$–$C_{12}$-alkyl, $C_5$–$C_9$-cycloalkyl, phenyl, $C_7$–$C_9$-aralkyl or a radical

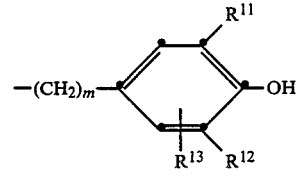

m is 0, 1 or 2 and n is 0 or 1 and, finally, $R^{11}$, $R^{12}$ and $R^{13}$ independently of one another are hydrogen or $C_1$–$C_{12}$-alkyl.

Compounds of the formula I which are also of interest are those in which $R^1$, $R^2$ and $R^3$ independently of one another are —C(R$^4$R$^5$)—(CHR$^6$)$_n$—W, —(CH$_2$)$_2$—OCOR$^{10}$ or a radical

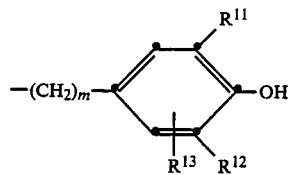

$R^4$, $R^5$ and $R^6$ independently of one another are hydrogen or methyl, and W is —COOR$^8$ or —CON(R$^9$R$^{15}$), R$^8$, R$^9$ and R$^{15}$ independently of one another being C$_1$–C$_{12}$-alkyl, cyclohexyl, phenyl, benzyl, tolyl or a radical

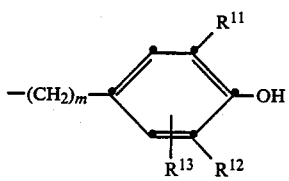

or R$^8$, R$^9$ and R$^{15}$ being C$_3$–C$_{12}$-alkyl which is interrupted by one to five —O— groups and is unsubstituted or substituted by a hydroxyl group, it being necessary for any oxygen atoms occurring several times to be separated by at least one methylene group, R$^{10}$ is C$_1$–C$_{12}$-alkyl, cyclohexyl, phenyl, benzyl or a radical

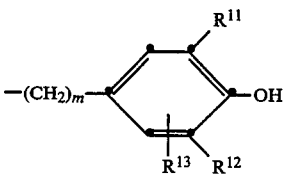

m is 0, 1 or 2 and n is 0 or 1 and R$^{11}$, R$^{12}$ and R$^{13}$ independently of one another are hydrogen or tert.-butyl.

Compounds of the formula I which are very particularly preferred are those in which R$^1$, R$^2$ and R$^3$ are —C(R$^4$R$^5$)—(CHR$^6$)$_n$—W, R$^4$, R$^5$ and R$^6$ independently of one another are hydrogen or methyl, W is —COOR$^8$ or —CON— (R$^9$R$^{15}$), and R$^8$, R$^9$ and R$^{15}$ independently of one another are C$_1$–C$_{12}$-alkyl, cyclohexyl, phenyl, benzyl, tolyl or a radical

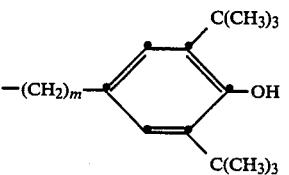

or are 2-hydroxyethyl, 2-hydroxypropyl, 3-oxabutyl or a radical —(CH$_2$—CH$_2$—O)$_p$—CH$_2$—CH$_2$—OH, p being 1, 2 or 3, or in which R$^9$ and R$^{15}$, together with the common nitrogen atom, form a piperidine or morpholine ring and in which m is 0, 1 or 2 and n is 0 or 1.

Compounds of the formula I which are also worthy of notice are those in which R$^1$, R$^2$ and R$^3$ are —(CH$_2$)$_2$—OCOR$^{10}$ and R$^{10}$ is C$_1$–C$_{12}$-alkyl, cyclohexyl, phenyl, benzyl or a radical

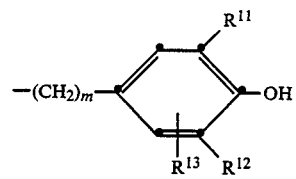

in which R$^{11}$, R$^{12}$ and R$^{13}$ independently of one another are hydrogen or tert.-butyl and in which m is 0, 1 or 2.

Compounds of the formula I which are also of interest are those in which R$^1$, R$^2$ and R$^3$ are a radical

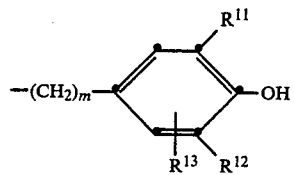

in which m is 0, 1 or 2 and R$^{11}$, R$^{12}$ and R$^{13}$ independently of one another are hydrogen or tert.-butyl.

The substances listed below can be regarded as examples of compounds of the formula I:

2,4,6-Tris-(2-hydroxyethylthiomethyl)-phenol, 2,4,6-tris-(2,3-dihydroxypropylthiomethyl)-phenol, the trimethyl ester of 2,4,6-tris-(3-carboxy-2-thiapropyl)-phenol, the triethyl ester of 2,4,6-tris-(3-carboxy-2-thiapropyl)-phenol, the tri-n-butyl ester of 2,4,6-tris-(3-carboxy-2-thiapropyl)-phenol, the tri-n-hexyl ester of 2,4,6-tris-(3-carboxy-2-thiapropyl)-phenol, the tri-n-octyl ester of 2,4,6-tris-(3-carboxy-3-thiapropyl)-phenol, the tri-(2-ethylhexyl)ester of 2,4,6-tris-(3-carboxy-2-thiapropyl)-phenol, the tri-n-decyl ester of 2,4,6-tris-(3-carboxy-2-thiapropyl)-phenol, the tri-n-dodecyl ester of 2,4,6-tris-(3-carboxy-2-thiapropyl)-phenol, the tri-n-tetradecylester of 2,4,6-tris-(3-carboxy-2-thiapropyl)-phenol, the tri-n-hexadecyl ester of 2,4,6-tris-(3-carboxy-2-thiapropyl)-phenol, the tri-n-octadecyl ester of 2,4,6-tris-(3-carboxy-2-thiapropyl)-phenol, the tri-n-eicosyl ester of 2,4,6-tris-(3-carboxy-2-thiapropyl)-phenol, the trioleyl ester of 2,4,6-tris-(3-carboxyl-2-thiapropyl)-phenol, the tricyclohexyl ester of 2,4,6-tris-(3-carboxy-2-thiapropyl)-phenol, the triphenyl ester of 2,4,6,-tris-(3-carboxy-2-thiapropyl)-phenol, the tribenzyl ester of 2,4,6-tris-(3-carboxy-2-thiapropyl)-phenol, the tri-α-methylbenzyl ester of 2,4,6-tris-(3-carboxy-2-thiapropyl)-phenol, the tri-(α,α-dimethylbenzyl)ester of 2,4,6-tris-(3-carboxy-2-thiapropyl)-phenol, the tri-p-tolyl ester of 2,4,6-tris-(3-carboxy-2-thiapropyl)-phenol, the tri-(3-oxabutyl)ester of 2,4,6-tris-(3-carboxy-2-thiapropyl)-phenol, the tri-(3-thiabutyl)ester of 2,4,6-tris-(3-carboxy-2-thiapropyl)-phenol, the tri-(N,N-dimethylamide) of 2,4,6-tris-(3-carboxy-2-thiapropyl)-phenol, the tri-(N,N-di-[2-ethylhexyl]-amide) of 2,4,6-tris-(3-carboxy-2-thiapropyl)-phenol, the triamide of 2,4,6-tris-(3-carboxy-2-thiapropyl)-phenol, 2,4,6-tri-(4-acetyl-2-thiabutyl)-phenol, 2,4,6-tri-(4-cyano-2-thiabutyl)-phenol, the trimethyl ester of 2,4,6-tris-(4-carboxy-2-thiabutyl)-phenol, the tri-n-octyl ester of 2,4,6-tris-(4-carboxyl-2-thiabutyl)-phenol, the tri-(2-ethylhexyl)ester of 2,4,6-tris-(4-carboxy-2-thiabutyl)-phenol, the tri-n-dodecyl ester of 2,4,6-tris-(4-carboxy-2-thiabutyl)-phenol, the tri-(2-ethylhexyl)ester of 2,4,6-tris-(4-carboxy-2-thiapentyl)-phenol, 2,4,6-tri-(4-acetoxy-2-thiabutyl)-phenol, 2,4,6-tri-(4-benzoyloxy-2-thiabutyl)-phenol, 2,4,6-tri-(4-cyclohexylcarbonyloxy-2- thiabutyl)-phenol, the tri-[N-(2-hydroxyethyl)]amide of 2,4,6-tris-(3- carboxy-2-thiapropyl)-phenol, the tri-(2-hydroxyethyl)ester of 2,4,6-tris-(3-carboxy-2-thiapropyl)-phenol, the tri-(N-piperidyl)amide of 2,4,6-tris-(3-carboxy-2-thiapropyl)phenol, 2,4,6-tris-(4-benzylcarbonyloxy-3-thiabutyl)-phenol, 2,4,6-tris-{4-[3-(4-hydroxy-3,5-di-tert.-butylphenyl)propionyloxy]-2-thiabutyl}-phenol, 2,4,6-tris-[4-(4-hydroxy-3,5-di-tert.-butylbenzylcarbonyloxy)-2-thiabutyl]-phenol, 2,4,6-tris-[4-(4-hydroxy-3,5-di-tert.-butylphenyl)-2-thiabutyl]-phenol.

The preparation of the compounds of the formula I is effected in accordance with processes known per se. Thus, for example, one molar fraction of phenol is reacted analogously to the description in British Patent Specification No. 1,184,533 with three molar fractions of formaldehyde and the corresponding amounts of suitably substituted mercaptans. It is also possible to use mixtures of different mercaptans.

The reaction can be carried out in the presence of absence of an organic solvent, in the presence of a basic catalyst, at temperatures between 70° C. and 150° C.

Suitable solvents are alcohols having one to six carbon atoms, for example methanol, ethanol, propanol, butanol, pentanol or hexanol. It is also possible, however, to use diols, polyols and ethers thereof, for example glycol, glycerol or polyethylene glycol. The reaction can also be carried out in polar, aprotic solvents, for example dimethylformamide or dimethyl sulfoxide, or high-boiling aromatic or aliphatic hydrocarbons, which can, if appropriate, be chlorinated, can be used, for example toluene, ligroin or chlorobenzene. The basic catalysts used are, for example, organic bases, such as dialkylamines or trialkylamines, or inorganic bases are used, such as hydroxides, preferably alkali metal hydroxides. However, it is only preferable to employ inorganic bases if the reactants do not contain hydrolysable groups, for example ester or amide groups.

Instead of formaldehyde, it is also possible to employ compounds which form formaldehyde under the reaction conditions. These include, for example, paraformaldehyde or hexamethylenetetramine.

The reaction mixure is heated under reflux for 5 to 40 hours under an atmosphere of nitrogen.

After cooling to room temperature, the organic phase is diluted with a suitable solvent, for example toluene, chloroform, methylene chloride, ether or methyl isobutyl ketone. The mixture is then washed with aqueous acid until it is neutral. Acetic acid, for example, can be employed for this purpose, but any other desired acid, for example a mineral acid, can also be used.

After the customary separation in vacuo, the organic phase is concentrated and the residue after evaporation is further purified, if necessary, for example by recrystallization, by column chromatography or by filtration through a short silica gel column.

The compounds of the formula I can, however, also be synthesised analogously to the process described in U.S. Pat. No. 4,091,037 by reacting a suitable tris-Mannich base and at least the stoichiometrical amount of a suitable mercaptan or a mixture of suitable mercaptans in the presence or absence of a suitable organic solvent and under an atmosphere of nitrogen. The reaction temperature is between 100° C. and 160° C.; the reaction time is 10 to 40 hours. The same organic solvents are suitable as for the variant described above. The reaction can be accelerated by applying a slight vacuum (0.1 to 0.6 bar). Working up is carried out as already described earlier in the text.

Compounds of the formula I in which $R^1$, $R^2$ or $R^3$ are the group $—CH_2CH_2—O—CO—R^{10}$ can preferably be prepared from the corresponding alcohol derivative in a known manner by esterification with an acid or acid chloride or by transesterification with a methyl or ethyl ester.

The invention also relates to compositions containing the organic material sensitive to thermal, oxidative or radiation-induced degradation and at least one compound of the formula I.

In a preferred embodiment, the compositions according to the invention contain mixtures of compounds of the formula I.

Compositions in which the organic material is a polymer, in particular an elastomer, a polyolefin or a styrene polymer, are also preferred. The following are particularly preferred as elastomers:

polydienes, for example polybutadiene, polyisoprene or polychloroprene; block polymers, for example styrene/butadiene/styrene, styrene/isoprene/styrene or styrene/ethylene-propylene/styrene types; and also acrylonitrile/butadiene polymers.

These polymers can also be in the form of latices and can be stabilised as such.

Compositions in which the organic material is a synthetic lubricant or a lubricant based on mineral oil are also preferred.

The lubricants which are suitable are familiar to those skilled in the art and are described, for example, in the "Schmiermittel Taschenbuch ["Lubricants Handbook"] (Hüthig Verlag, Heidelberg, 1974)".

The invention also relates to the use of compounds of the formula I as stabilisers for organic material against damage caused to the latter by the action of oxygen, heat, light and high-energy radiation.

Preferred uses of the compounds are as antioxidants in organic polymers, particularly in polyolefins, styrene polymers or elastomers, or their use in mineral oils or synthetic oils.

The compounds according to the invention are also suitable for use as EP/AW additives for lubricants or metal-working fluids.

The following are further examples of organic material which can advantageously be stabilised by means of the compounds according to the invention:
1. Polymers of monoolefins and diolefins, for example polyethylene (which can, if desired, be crosslinked), polypropylene, polyisobutylene, polybut-1-ene, polymethylpent-1-ene, polyisoprene or polybutadiene, and also polymers of cycloolefins, for example polymers of cyclopentene or norbornene.
2. Mixtures of the polymers mentioned under (1), for examples mixtures of polypropylene and polyisobutylene.
3. Copolymers of monoolefins and diolefins with one another or with other vinyl monomers, for example ethylene/propylene copolymers, propylene/but-1-ene copolymers, propylene/isobutylene copolymers, ethylene/but-1-ene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and salts thereof (ionomers), and also terpolymers of ethylene with propylene and a diene, such as hexadiene, dicyclopentadiene or ethylidenenorbornene.

4. Polystyrene and poly-(p-methylstyrene).
5. Copolymers of styrene or α-methylstyrene with dienes or acrylic derivatives, for example styrene/butadiene, styrene/acrylonitrile, styrene/alkyl methacrylate, styrene/maleic anhydride or styrene/acrylonitrile/methyl acrylate; mixtures of high impact strength formed from styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene or styrene-/ethylene-propylene/styrene.
6. Graft copolymers of styrene, for example styrene on polybutadiene, styrene and acrylonitrile on polybutadiene, styrene and maleic anhydride on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkylmethacrylates, styrene and acrylonitrile on acrylate/butadiene copolymers and mixtures thereof with the copolymers mentioned under (5) such as are known, for example, as so-called ABS, MBS, ASA or AES polymers.
7. Halogen-containing polymers, for example polychloroprene, chlorinated rubber, chlorinated or chlorosulfonated polyethylene and epichlorohydrin homopolymers and copolymers, in particular polymers formed from halogen-containing vinyl compounds, for example polyvinyl chloride, polyvinylidene chloride, polyvinyl fluoride and polyvinylidene fluoride; and also copolymers thereof, such as vinyl chloride/vinylidene chloride, vinyl chloride/vinyl acetate or vinylidene chloride/vinyl acetate.
8. Polymers derived from α,β-unsaturated acids and derivatives thereof, such as polyacrylates and polymethacrylates, polyacrylamides and polyacrylonitriles.
9. Copolymers of the monomers mentioned under (8) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.
13. Polyphenyl oxides and sulfides and mixtures thereof with styrene polymers.
14. Polyurethanes derived from polyethers, polyesters and polybutadienes having terminal hydroxyl groups on the one hand and from aliphatic or aromatic polyisocyanates on the other hand, and also precursors thereof.
15. Polyamides and copolyamides derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethyleneterephthalamide and poly-m-phenyleneisophthalamide, and block copolymers thereof with polyethers, for example polyethylene glycol, polypropylene glycol or polytetramethylene glycol.
16. Polyureas, polyimides, polyamide-imides and polybenzimidazoles.
17. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate and polyhydroxybenzoates, and block polyether-esters derived from polyethers containing hydroxyl end groups.
18. Polycarbonates and polyester-carbonates.
19. Polysulfones, polyether-sulfones and polyether-ketones.
20. Crosslinked polymers derived from aldehydes on the one hand and from phenols, urea or melamine on the other hand, such as phenol/formaldehyde, urea-/formaldehyde and melamine/formaldehyde resins.
21. Drying and non-drying alkyd resins.
22. Unsaturated polyester resins derived from copolyesters of saturated and unsaturated dicarboxylic acids with polyhydric alcohols, and from vinyl compounds as crosslinking agents, and also halogen-containing modifications thereof of low flammability.
23. Crosslinkable acrylic resins derived from substituted acrylic acid esters, for example from epoxyacrylates, urethane-acrylates or polyester-acrylates.
24. Alkyd resins, polyeeser resins and acrylate resins which have been crosslinked with melamine resins, urea resins, polyisocyanates or epoxide resins.
25. Crosslinked epoxide resins derived from polyepoxides, for example from bisglycidyl ethers or from cycloaliphatic diepoxides.
26. Natural polymers, such as cellulose, natural rubber and gelatine and polymer-homologously chemically modified derivatives thereof, such as cellulose acetates, propionates and butyrates, and the cellulose ethers, such as methylcellulose.
27. Mixtures (polyblends) of the abovementioned polymers, for example PP/EPDM, polyamide 6/EPDM or ABS, PVC/EVA, PVC/ABS, PVC/MBS, PC/ABS or PBTP/ABS.
28. Natural and synthetic organic substances which are pure monomeric compounds or mixtures thereof, for example mineral oils, animal or vegetable fats, oils and waxes, or oils, waxes and fats based on synthetic esters (for example phthalates, adipates, phosphates or trimellitates), and mixtures of synthetic esters and mineral oils in any desired ratios by weight, such as are used, for example, as spinning dressings, and also aqueous emulsions thereof.
29. Aqueous emulsions of natural or synthetic rubbers, for example natural rubber latex or latices of carboxylated styrene/butadiene copolymers.

The stabilisers are added to the plastics or lubricants in a concentration of 0.01–10% by weight, calculated on the material to be stabilised. It is preferable to incorporate 0.05 to 5.0% by weight, particularly preferentially 0.1 to 2.0% by weight, of the compounds into the material to be stabilised, calculated on the latter.

The incorporation can be effected, for example, by mixing in the substances of the formula I and, if appropriate, further additives in accordance with the methods customary in the state of the art, before or during shaping, or by applying the dissolved or dispersed compounds to the polymer, if appropriate with subsequent evaporation of the solvent. The novel compounds can also be added to the plastics to be stabilised in the form of a master batch containing these compounds in a concentration of, for example, 2.5 to 25% by weight.

In the case of crosslinkable polyethylene, the compounds are added before crosslinking.

The materials thus stabilised can be used in a very wide variety of forms, for example as sheeting, fibres, tapes, moulding compositions or profiles or as binders for lacquers, adhesives or putties.

In practice, the phenols of the formula I can be employed in conjunction with other stabilisers.

Lubricant formulations can, in addition, also contain other additives which are added in order to improve certain properties in use, for example further antioxidants, metal passivators, rust inhibitors, viscosity index improvers, pour-point depressants, dispersants/surfactants and antiwear additives.

The following may be mentioned as examples of further additives in conjunction with which the stabilisers used in accordance with the invention can be employed:

1. ANTIOXIDANTS

1.1 Alkylated monophenols 2,6-Di-tert.-butyl-4-methylphenol, 2-tert.-butyl-4,6-dimethylphenol, 2,6-di-tert.-butyl-4-ethylphenol, 2,6-di-tert.-butyl-4-n-butylphenol, 2,6-di-tert.-butyl-4-i-butylphenol, 2,6-di-cyclopentyl-4-methylphenol, 2-(α-methylcyclohexyl)-4,6-dimethylphenol, 2,6-di-octadecyl-4-methylphenol, 2,4,6-tricyclohexylphenol and 2,6-di-tert.-butyl-4-methoxymethylphenol.

1.2 Alkylated hydroquinones 2,6-Di-tert.-butyl-4-methoxyphenol, 2,5-di-tert.-butyl-hydroquinone, 2,5-di-tert.-amyl-hydroquinone and 2,6-diphenyl-4-octadecyloxyphenol.

1.3 Hydroxylated thiodiphenyl ethers 2,2'-Thio-bis-(6-tert.-butyl-4-methylphenol), 2,2'-thio-bis-(4-octylphenol), 4,4'-thio-bis-(6-tert.-butyl-3-methylphenol) and 4,4'-thio-bis-(6-tert.-butyl-2-methylphenol).

1.4 Alkylidene-bisphenols 2,2'-Methylene-bis-(6-tert.-butyl-4-methylphenol), 2,2'-methylene-bis-(6-tert.-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert.-butylphenol), 2,2'-ethylidene-bis-(4,6-di-tert.-butylphenol), 2,2'-ethylidene-bis-(6-di-tert.-butyl-4-isobutylphenol), 2,2'-methylene-bis-[6-(α-methylbenzyl)-4-nonylphenol], 2,2'-methylene-bis-[6-(α,α-dimethylbenzyl)-4-nonylphenol], 4,4'-methylene-bis-(2,6-di-tert.-butylphenol), 4,4'-methylene-bis-(6-tert.-butyl-2-methylphenol), 1,1-bis-(5-tert.-butyl-4-hydroxy-2-methylphenyl)-butane, 2,6-di-(3-tert.-butyl-5-methyl-2-hydroxybenzyl)-4-methylphenol, 1,1,3-tris-(5-tert.-butyl-4-hydroxy-2-methylphenyl)-butane, 1,1-bis(5-tert.-butyl-4-hydroxy-2-methylphenyl)-3-n-dodecylmercaptobutane, ethylene glycol bis-[3,3-bis-(3'-tert.-butyl-4'-hydroxyphenyl)butyrate], di-(3-tert.-butyl-4-hydroxy-5-methylphenyl)-dicyclopentadiene, di-[2-(3'-tert.-butyl-2'-hydroxy-5'-methylbenzyl)-6-tert.-butyl-4-methyl-phenyl]terephthalate.

1.5 Benzyl compounds 1,3,5-Tri-(3,5-di-tert.-butyl-4-hydroxybenzyl)-2,4,6-trimethylbenzene, di-(3,5-di-tert.-butyl-4-hydroxybenzyl)sulfide, isooctyl 3,5-ditert.-butyl-4-hydroxybenzylmercaptoacetate, bis-(4-tert.-butyl-3-hydroxy-2,6-dimethylbenzyl)-dithiol terephthalate, 1,3,5-tris-(3,5-di-tert.-butyl-4-hydroxybenzyl)isocyanurate, 1,3,5-tris-(4-tert.-butyl-3-hydroxy-2,6-dimethylbenzyl)isocyanurate, di-octadecyl 3,5-di-tert.-butyl-4-hydroxybenzyl phosphonate and the calcium salt of monoethyl 3,5-di-tert.-butyl-4-hydroxybenzyl phosphonate.

1.6 Acylamino phenols

4-Hydroxylauranilide, 4-hydroxystearanilide, 2,4-bis-octylmercapto-6-(3,5-di-tert.-butyl-4-hydroxyanilino)-s-triazine and octyl N-(3,5-di-tert.-butyl-4-hydroxyphenyl)-carbamate.

1.7 Esters of β-(3,5-di-tert.-butyl-4-hydroxyphenyl)-propionic acid with monohydric or polyhydric alcohols, for example with: methanol, octadecanol, 1,6-hexanediol, neopentylglycol, thiodiethylene glycol, diethylene glycol, triethylene glycol, pentaerythritol, trishydroxyethyl isocyanurate and dihydroxyethyloxamide.

1.8 Ester of β-(5-tert.-butyl-4-hydroxy-3-methylphenyl)-propionic acid with monohydric or polyhydric alcohols, for example with: methanol, octadecanol, 1,6-hexanediol, neopentylglycol, thiodiethylene glycol, diethylene glycol, triethylene glycol, pentaerythritol, trishydroxyethyl isocyanurate and dihydroxyethyloxamide.

1.9 Amides of β-(3,5-di-tert.-butyl-4-hydroxyphenyl)-propionic acid, for example, N,N'-di-(3,5-di-tert.-butyl-4-hydroxyphenylpropionyl)-hexamethylenediamine, N,N'-di-(3,5-di-tert.-butyl-4-hydroxyphenylpropionyl)-trimethylenediamine and N,N'-di-(3,5-di-tert.-butyl-4-hydroxyphenylpropionyl)-hydrazine.

2. UV ABSORBERS AND LIGHT STABILISERS

2.1 2-(2'-Hydroxyphenyl)-benztriazoles, for example the 5'-methyl-, 3',5'-di-tert.-butyl-, 5'-tert.-butyl-, 5'-(1,1,3,3-tetramethylbutyl)-, 5-chloro-3',5'-ditert.-butyl-, 5-chloro-3'-tert.-butyl-5'-methyl-, 3'-sec.-butyl-5'-tert.-butyl, 4'-octoxy-, 3',5'-di-tert.-amyl- and 3',5'-bis-(α,α-dimethylbenzyl)-derivative.

2.2 2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy-derivative.

2.3 Ester of substituted or unsubstituted benzoic acids, for example 4-tert.-butyl-phenyl salicylate, phenyl salicylate, octylphenyl salicylate, dibenzoylresorcinol, bis-(4-tert.-butylbenzoyl)-resorcinol, benzoylresorcinol, 2,4-di-tert.-butylphenyl 3,5-di-tert.-butyl-4-hydroxybenzoate and hexadecyl 3,5-di-tert.-butyl-4-hydroxybenzoate.

2.4 Acrylates, for example ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate and N-(β-carbomethoxy-β-cyanovinyl)-2-methylindoline.

2.5 Nickel compounds, for example nickel complexes of 2,2'-thiobis-[4-(1,1,3,3-tetramethylbutyl)-phenol], such as the 1:1 or 1:2 complex, if desired containing additional ligands, such as n-butylamine, triethanolamine or N-cyclohexyldiethanolamine, nickel dibutyldithiocarbamate, nickel salts of 4-hydroxy-3,5-di-tert.-butylbenzylphosphonic acid monoalkyl esters, such as the methyl or ethyl ester, nickel complexes of ketoximes, such as 2-hydroxy-4-methylphenylundecyl ketone oxime and nickel complexes of 1-phenyl-4-lauroyl-5-hydroxypyrazole, if desired containing additional ligands.

2.6 Stearically hindered amines, for example bis-(2,2,6,6-tetramethylpiperidyl)sebacate, bis-(1,2,2,6,6-pentamethylpiperidyl)sebacate, bis-(1,2,2,6,6-pentamethylpiperidyl) n-butyl-3,5-di-tert.-butyl-4-hydroxybenzylmalonate, the condensation product formed from 1-hydroxyethyl-2,2,6,6-tetramethyl-4-hydroxypiperidine and succinic acid, the condensation product formed from N,N'-(2,2,6,6-tetramethyl-4-piperidyl)-hexamethylenediamine and 4-tert.-octylamino-2,6-dichloro-1,3,5-s-triazine, tris-(2,2,6,6-tetramethyl-4-piperidyl)nitrilotriacetate, tetrakis-(2,2,6,6-tetramethyl-4-piperidyl)-1,2,3,4-butanetetracarboxylate and 1,1'-(1,2-ethanediyl)-bis-(3,3,5,5-tetramethyl piperazinone).

2.7 Oxamides, for example 4,4'-dioctyloxyoxanilide, 2,2'-dioctyloxy-5,5'-di-tert.-butyloxanilide, 2,2'-didodecyloxy-5,5'-di-tert.-butyloxanilide, 2-ethoxy-2'-ethyloxanilide, N,N'-bis-(3-dimethylaminopropyl)-oxamide, 2-ethoxy-5-tert.-butyl-2'-ethyloxanilide and a mixture thereof with 2-ethoxy-2'-ethyl-5,4'-di-tert.-butyloxanilide and mixtures of ortho-methoxy- and para-methoxy-disubstituted oxanilides and of o-ethoxy- and p-ethoxy-disubstituted oxanilides.

3. Metal deactivators, for example N,N'-diphenyloxamide, N-salicylal-N'-salicyloylhydrazine, N,N'-bis-salicyloylhydrazine, N,N'-bis-(3,5-di-tert.-butyl-4-hydroxyphenylpropionyl)-hydrazine, 3-salicyloylamino-1,2,4-triazole and bis-benzylideneoxalic acid dihydrazide.

4. Phosphites and phosphonites, for example triphenyl phosphite, diphenylalkyl phosphites, phenyldialkyl phosphites, tri-(nonylphenyl)-phosphite, trilauryl phosphite, trioctadecyl phosphite, distearylpentaerythritol diphosphite, tris-(2,4-di-tert.-butylphenyl)phosphite, diisodecylpentaerythritol diphosphite, di-(2,4-di-tert.-butylphenyl)-pentaerythritol diphosphite, tristearylsorbityl triphosphite and tetrakis-(2,4-di-tert.-butylphenyl) 4,4'-biphenylenediphosphonite.

5. Compounds which destroy peroxides, for example esters of β-thiodipropionic acid, for example the lauryl, stearyl, myristyl or tridecyl ester, mercaptobenzimidazole, the zinc salt of 2-mercaptobenzimidazole, zinc dibutyldithiocarbamate, dioctadecyl disulfide and pentaerythritol tetrakis-(β-dodecylmercapto)-propionate.

6. Polyamide stabilisers, for example copper salts in combination with iodides and/or phosphorus compounds, and salts of divalent manganese.

7. Basic co-stabilisers, for example melamine, polyvinylpyrrolidone, dicyandiamide, triallyl cyanurate, urea derivetives, hydrazine derivatives, amines, polyamides, polyurethanes, alkali and alkaline earth metal salts of higher fatty acids, for example Ca stearate, Zn stearate, Mg stearate, Na ricinoleate or K palmitate, antimony pyrocatecholate or tin pyrocatecholate.

8. Nucleating agents, for example 4-tert.-butylbenzoic acid, adipic acid or diphenylacetic acid.

9. Fillers and reinforcing agents, for example calcium carbonate, silicates, glass fibres, asbestos, talc, kaolin, mica, barium sulfate, metal oxides and hydroxides, carbon black or graphite.

10. Other additives, for example plasticisers, slip agents, emulsifiers, pigments, fluorescent brighteners, flame-proofing agents, antistatic agents or blowing agents.

11. Amine antioxidants:

N,N'-diisopropyl-p-phenylenediamine, N,N'-di-sec.-butyl-p-phenylenediamine, N,N'-bis-(1,4-dimethylpentyl)-p-phenylenediamine, N,N'-bis-(1-ethyl-3-methylpentyl)-p-phenylendiamine, N,N'-bis-(1-methylheptyl)-p-phenylendiamine, N,N'-dicyclohexyl-p-phenyldiamine, N,N'-diphenyl-p-phenyldiamine, N,N'-di-(naphth-2-yl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamido)-diphenylamine, N,N'-dimethyl-N,N'-di-sec.-butyl-p-phenylenediamine, diphenylamine, 4-isopropoxydiphenylamine, N-phenyl-1-naphthylamine, N-phenyl-2-naphthylamine, octylated diphenylamine, 4-n-butylaminophenol, 4-butyrylaminophenol, 4-nonanoylaminophenol, 4-dodecanoylaminophenol, 4-octadecanoylaminophenol, di-(4-methoxyphenyl)-amine, 2,6-di-tert.-butyl-4-dimethylaminomethylphenol, 2,4'-diaminodiphenylmethane, 4,4'-diaminodiphenylmethane, N,N,N,N'-tetramethyl-4,4'-diaminodiphenylmethane, 1,2-di-(phenylamino)-ethane, 1,2-di-[(2-methylphenyl)-amino]-ethane, 1,3-di-(phenylamino)-propane, (o-tolyl)-biguanide and di-[4-(1',3'-dimethylbutyl)-phenyl]-amine.

12. Metal passivators:

for copper, for example benztriazole, tetrahydrobenztriazole, 2-mercaptobenzthiazole, 2,5-dimercaptothiadiazole, salicylidenepropylenediamine and salts of salicylaminoguanidine.

13. Rust inhibitors:

(a) organic acids and esters, metal salts and anhydrides thereof, for example: N-oleoylsarcosine, sorbitan monooleate, lead naphthenate, dodecenylsuccinic anhydride, alkenylsuccinic acid half esters or 4-nonylphenoxyacetic acid.

(b) Nitrogen-containing compounds, for example:
I. Primary, secondary or tertiary aliphatic or cycloaliphatic amines and amine salts of organic and inorganic acids, for example oil-soluble alkylammonium carboxylates.

II. Heterocyclic compounds, for example: substituted imidazolines and oxazolines.

(c) Phosphorus-containing compounds, for example: amine salts of phosphoric acid partial esters.

(d) Sulfur-containing compounds, for example: barium dinonylnaphthalenesulfonates or calcium petroleum sulfonates.

14. Viscosity index improvers:

polymethacrylates, vinylpyrrolidone/methacrylate copolymers, polybutenes, olefin copolymers or styrene/acrylate copolymers.

15. Pour-point depressants: polymethacrylate or alkylated naphthalene derivatives.

16. Dispersants/surfactants:

polybutenylsuccinic acid imides, polybutenylphosphonic acid derivatives or basic magnesium, calcium and barium sulfonates and phenates.

17. Anti-wear additives:

compounds containing sulfur and/or phosphorus and/or halogen, such as sulfurised vegetable oils, zinc dialkyldithiophosphates, tritolyl phosphate, chlorinated paraffins or alkyl and aryl disulfides.

PREPARATION EXAMPLES

Example 1

26.5 g (0.1 mole) of 2,4,6-tris-(dimethylaminomethyl)-phenol and 61.6 g (0.3 mole) of 2-ethylhexyl thioglycollate are mixed at room temperature and are heated at 140° C. for 10 hours under a gentle stream of nitrogen. The mixture is then completely degassed in a high vacuum (0.7 mbar) for 2 hours at 80°. The residue is purified further by column chromatography; 2,4,6,-tris-[(2-ethylhexyloxycarbonyl)-methylthiomethyl]-phenol is obtained in the form of a clear, yellowish oil: Calc. S. 12.94%, found S 13.07% (characteristic $^1$H-NMR signals in Table 1).

Example 2

The same compound is obtained is 9.4 g of phenol, 61.3 g of 2-ethylhexyl thioglycollate, 9 g of paraformaldehyde, 30 ml of dimethylformamide and 2.4 g of dibutylamine are heated at 130° for 8 hours under a gentle stream of nitrogen, freed from solvent on a rotary evaporator and then worked up further as described in Example 1.

Example 3

The procedure described in Example 1 is followed, except that the corresponding amount of 2-ethylhexyl 3-mercaptopropionate is employed instead of 2-ethylhexyl thioglycollate. 2,4,6-tris-[(2-(2-ethylhexyl)-oxycarbonylethyl)-thiomethyl]-phenol is obtained in the form of a yellowish liquid. Calc. S 12.25%, found S 12.38% (characteristic $^1$H-NMR signals in Table 1).

Example 4

The procedure described in Example 1 is followed, except that the corresponding amount of stearyl thioglycollate is employed instead of 2-ethylhexyl thioglycollate. 2,4,6-tris-(stearyloxycarbonylmethylthiomethyl)-phenol of melting point 70°-71° C. is obtained. Calc. S 8.26%, found S 8.34% (characteristic $^1$H-NMR signals in Table 1).

Example 5

The procedure described in Example 1 is followed, except that the corresponding amount of 2-mercaptoethanol is employed instead of 2-ethylhexyl thioglycollate. 2,4,6-tris-(2-hydroxyethylthiomethyl)-phenol is obtained in the form of a yellowish oil. Calc. S 26.38%, found 26.40% (characteristic $^1$H-NMR signals in Table 1).

TABLE 1

Characteristic $^1$H—NMR signals of the compounds claimed[1]

| Example No. | $R^1=R^2=R^3$ | Signal of aryl-CH$_2$—S ortho-CH$_2$ (ppm) | para-CH$_2$ (ppm) | Equipment used |
|---|---|---|---|---|
| 1 | CH$_2$COOCH$_2$CH(C$_2$H$_5$)—(CH$_2$)$_3$—CH | 3.80 | 3.67 | (a) |
| 3 | CH$_2$CH$_2$COOCH$_2$CH(C$_2$H$_5$)—(CH)$_3$—CH$_3$ | 3.72 | 3.60 | (a) |
| 4 | CH$_2$COO(CH$_2$)$_{17}$—CH$_3$ | 3.80 | 3.67 | (a) |
| 5 | CH$_2$CH$_2$OH | 3.85 | 3.70 | (b)[2] |

(a) 60 MHz
(b) 100 MHz
[1] recorded in CDCl$_3$, using TMS as standard
[2] in d$_6$-acetone

USE EXAMPLES

Example 6

TFOUT test (thin-film oxygen uptake test)

This test is a modified version of the "rotary bomb oxidation test for mineral oils" (ASTM D 2272). It is described in detail in "C. S. Ku and S. M. Hsu, A Thin-Film Oxygen Uptake Test for Evaluation of Automotive Crankcase Lubricants, Lubrication Engineering, volume 40 (2), 75-83 (1984)". The test oil used is an engine oil based on mineral oil, containing half the customary amount of zinc dithiophosphate (0.75%; zinc content 0.06%, relative to the engine oil).

The compound prepared in Example 1 is tested in the engine oil described, in the presence of 2% of water, a liquid, oxidised, nitrated fraction of an engine oil as catayst (employed in a concentration of 4%) and a liquid metal naphthenate as a further catalyst (employed in a concentration of 4%; the water and the two liquid catalyst substances were supplied with an analytical certificate under the standard reference material No. 1817 of the National Bureau of Standards (NBS)). The test is complete at a pronounced point of flexion in the pressure/time diagram. The results quoted in the table below denote the time (in minutes) elapsed before the point of flexion in the pressure/time diagram.

Long times correspond to a good stabilising activity. Concentration of the stabiliser: 0.5% by weight, relative to the oil.

| Stabiliser | Minutes elapsed before pronounced decrease in pressure |
|---|---|
| none | 76 |

| Stabiliser | Minutes elapsed before pronounced decrease in pressure |
|---|---|
| Example 1 | 128 |

What is claimed is:

1. A compound of the formula I

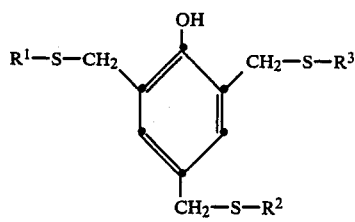

in which $R^1$, $R^2$ and $R^3$ independently of one another are $C_2$–$C_{20}$-alkyl, —$C(R^4R^5)$ which is substituted by one or two hydroxyl groups, or are —$C(R^4R^5)$—$(CHR^6)_n$—W or —$(CH_2)_2$—$OCOR^{10}$ or are a radical

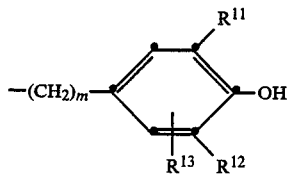

in which $R^4$, $R^5$ and $R^6$ independently of one another are hydrogen, $C_1$–$C_6$-alkyl, phenyl or cyclohexyl, W is —$COR^7$, —$COOR^8$, —$CON(R^9R^{15})$ or —CN, $R^7$ being hydrogen, $C_1$–$C_{20}$-alkyl, $C_5$–$C_{12}$-cycloalkyl, phenyl, 1-naphthyl, 2-naphthyl, $C_7$–$C_{14}$-aralkyl or $C_7$–$C_{14}$-alkaryl, $R^8$ being $C_1$–$C_{20}$-alkyl, $C_5$–$C_{12}$-cycloalkyl, phenyl, 1-naphthyl, 2-naphthyl, $C_7$–$C_{14}$-aralkyl, $C_7$–$C_{14}$-alkaryl or $C_2$–$C_{20}$-alkyl which is substituted by a hydroxyl or cyano group, or $C_2$–$C_{12}$-alkenyl, $C_2$–$C_{12}$-alkenyl or phenyl which is substituted by one or two —$NO_2$, —Cl, —Br, —$OCH_3$ or —$COOR^{14}$ groups, or a radical

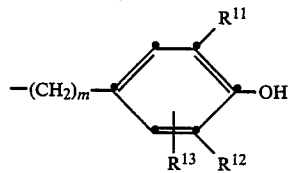

or $C_3$–$C_{20}$-alkyl which is interrupted by one to five —O—, —S—, —$N(CH_3)$—, —$N(C_2H_5)$— or —$SO_2$— groups and is unsubstituted or substituted by a hydroxyl group, it being necessary for any hetero-atoms occurring several times to be separated by at least one methylene group, $R^9$ having one of the meanings of $R^8$ or being additionally hydrogen, $R^{15}$ having one of the meanings of $R^9$, or $R^9$ and $R^{15}$, together with the common nitrogen atom, forming a 5-membered, 6-membered or 7-membered, heterocyclic ring which can also contain a further hetero-atom, $R^{10}$ being $C_1$–$C_{20}$-alkyl, $C_5$–$C_{12}$-cycloalkyl, phenyl, 1-naphthyl, 2-naphthyl, $C_7$–$C_{14}$-aralkyl, $C_7$–$C_{14}$-alkaryl or a radical

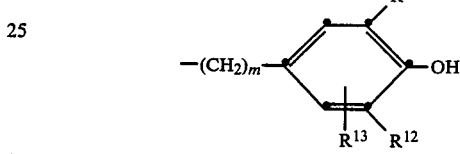

m being 0, 1 or 2, n being 0 or 1, $R^{11}$, $R^{12}$ and $R^{13}$ independently of one another being hydrogen, $C_1$–$C_{20}$-alkyl, cyclohexyl or phenyl and, $R^{14}$ being $C_1$–$C_6$-alkyl, phenyl, cyclohexyl, benzyl or tolyl.

2. A compound of the formula I, according to claim 1, in which $R^1$, $R^2$ and $R^3$ independently of one another are 2-hydroxyethyl, 2-hydroxypropyl or 2,3-dihydroxypropyl.

3. A compound of the formula I, according to claim 1, in which $R^1$, $R^2$ and $R^3$ independently of one another are —$C(R^4R^5)$—$(CHR^6)_n$—W, —$(CH_2)_2$—$OCOR^{10}$ or a radical

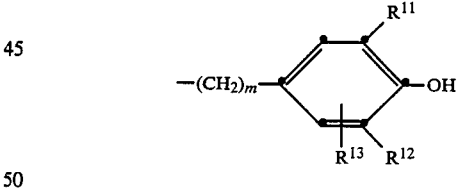

and the symbols $R^4$, $R^5$, $R^6$, $R^{10}$, $R^{11}$, $R^{12}$, $R^{13}$, W, m and n are as defined in claim 1.

4. A compound of the formula I, according to claim 3, in which $R^4$, $R^5$ and $R^6$ independently of one another are hydrogen or methyl, $R^7$ is $C_1$–$C_{12}$-alkyl, $C_5$–$C_9$-cycloalkyl, phenyl, benzyl, or tolyl, $R^8$, $R^9$ and $R^{15}$ independently of one another have the same meaning as $R^7$ or additionally are 2-hydroxyethyl, 2-hydroxypropyl, 2-cyanoethyl, allyl, propargyl or phenyl which is substituted by —Cl, —$COOCH_3$ or —$OCH_3$ or are a radical

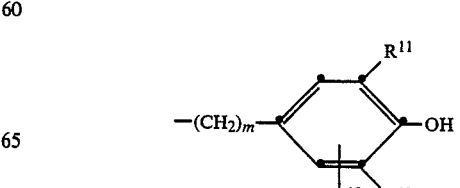

or $R^8$, $R^9$ and $R^{15}$ are $C_3$–$C_{12}$-alkyl which is interrupted by one to five —O— groups and is unsubstituted or substituted by a hydroxyl group, it being necessary for an oxygen atoms occurring several times to be separated by at least one methylene group, or $R^9$ and $R^{15}$, together with the common nitrogen atom, form a pyrrole, piperidine, pyrrolidine or morpholine ring, $R^{10}$ is $C_1$–$C_{12}$-alkyl, $C_5$–$C_9$-cycloalkyl, phenyl, $C_7$–$C_9$-aralkyl or a radical m is 0, 1 or 2 and, $R^{11}$, $R^{12}$ and $R^{13}$ independently of one another are hydrogen or $C_1$-$C_{12}$-alkyl.

5. A compound of the formula I, according to claim 1, in which $R^4$, $R^5$ and $R^6$ independently of one another are hydrogen or methyl, W is —$COOR^8$ or —$CON(R^9R^{15})$, $R^8$, $R^9$ and $R^{15}$ independently of one another are $C_1$-$C_{12}$-alkyl, cyclohexyl, phenyl, benzyl, tolyl or a radical

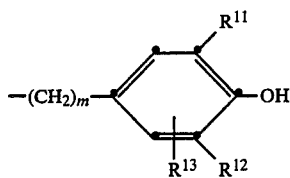

or in which $R^8$, $R^9$ and $R^{15}$ are $C_3$-$C_{12}$-alkyl which is interrupted by one to five —O— groups and is unsubstituted or substituted by a hydroxyl group, it being necessary for any oxygen atoms occurring several times to be separated by at least one methylene group, and in which $R^{10}$ is $C_1$-$C_{12}$-alkyl, cyclohexyl, phenyl, benzyl or a radical

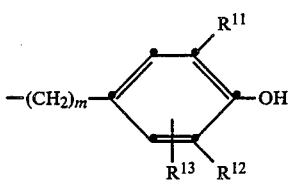

m is 0, 1 or 2 and $R^{11}$, $R^{12}$ and $R^{13}$ independently of one another are hydrogen or tert.-butyl.

6. A compound of the formula I, according to claim 1, in which $R^1$, $R^2$ and $R^3$ are —$C(R^4R^5)$—$(CHR^6)_n$—W in which $R^4$, $R^5$ and $R^6$ independently of one another are hydrogen or methyl, W is —$COOR^8$ or —$CON(R^9R^{15})$, $R^8$, $R^9$ and $R^{15}$ independently of one another are $C_1$-$C_{12}$-alkyl, cyclohexyl, phenyl, benzyl, tolyl or a radical

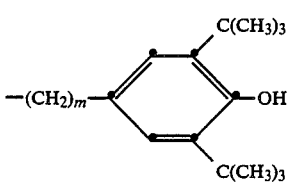

or are 2-hydroxyethyl, 2-hydroxypropyl, 3-oxabutyl or a radical —$(CH_2$—$CH_2$—$O)_p$—$CH_2$—$CH_2$—OH, p being 1, 2 or 3, and m and n are as defined in claim 1, or in which $R^9$ and $R^{15}$, together with the common nitrogen atom, from a piperidine or morpholine ring.

7. A compound of the formula I, according to claim 1, in which $R^1$, $R^2$ and $R^3$ are —$(CH_2)_2$—$OCOR^{10}$ and $R^{10}$ is $C_1$-$C_{12}$-alkyl, cyclohexyl, phenyl, benzyl or a radical

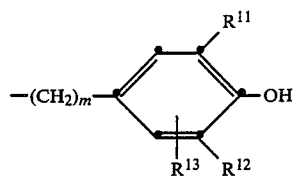

in which $R^{11}$, $R^{12}$ and $R^{13}$ independently of one another are hydrogen or tert.-butyl and m is 0, 1 or 2.

8. A compound of the formula I, according to claim 1, in which $R^1$, $R^2$ and $R^3$ are radicals of the formula

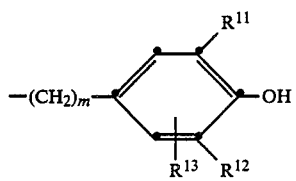

in which $R^{11}$, $R^{12}$ and $R^{13}$ independently of one another are hydrogen or tert.-butyl and m is 0, 1 or 2.

9. A compound of the formula I, according to claim 1, in which $R^1$, $R^2$ and $R^3$ are the radical

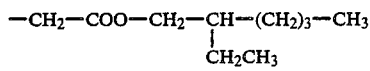

10. A lubricant composition which comprises
(a) a lubricant, and
(b) 0.01 to 10% by weight, based on component (a) of at least one compound of formula I

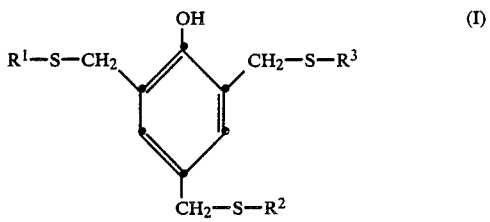

in which $R^1$, $R^2$ and $R^3$ independently of one another are $C_2$-$C_{20}$-alkyl which is substituted by one or two hydroxyl groups, or are —$C(R^4R^5)$—$(CHR^6)_n$—W or —$(CH_2)_2$—$OCOR^{10}$, or are a radical

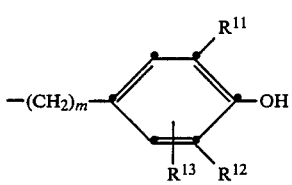

in which $R^4$, $R^5$ and $R^6$ independently of one another are hydrogen, $C_1$-$C_6$-alkyl, phenyl or cyclohexyl, W is —$COR^7$, —$COOR^8$, —$CON(R^9R^{15})$ or —CN, $R^7$ being hydrogen, $C_1$-$C_{20}$-alkyl, $C_5$-$C_{12}$-cycloalkyl, phenyl, 1-naphthyl, 2-naphthyl, $C_7$-$C_{14}$-aralkyl or $C_7$-$C_{14}$-alkaryl, $R^8$ being $C_1$-$C_{20}$-alkyl, $C_5$-$C_{12}$-cycloalkyl, phenyl, 1-naphthyl, 2-naphthyl, $C_7$-$C_{14}$-aralkyl, $C_7$-$C_{14}$-alkaryl or $C_2$-$C_{20}$-alkyl which is substituted by a hydroxyl or cyano group, or $C_2$-$C_{12}$-alkenyl, $C_2$-$C_{12}$-alkinyl or phenyl which is substituted by one or two —NO$_2$, —Cl, —Br, —OCH$_3$ or —COOR$^{14}$ groups, or a radical

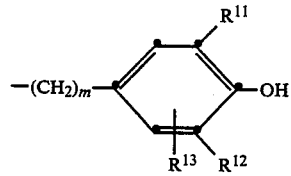

or C$_3$–C$_{20}$-alkyl which is interrupted by one to five —O—, —S—, —N(CH$_3$)—, —N(C$_2$H$_5$)— or —SO$_2$— groups and is unsubstituted or substituted by a hydroxyl group, it being necessary for any hetero-atoms occurring several times to be separated by at least one methylene group, R$^9$ having one of the meanings of R$^8$ or being additionally hydrogen, R$^{15}$ having one of the meanings of R$^9$, or R$^9$ and R$^{15}$, together with the common nitrogen atom, forming a 5-membered, 6-membered or 7-membered, heterocyclic ring which can also contain a further hetero-atom, R$^{10}$ being C$_1$–C$_{20}$-alkyl, C$_5$–C$_{12}$-cycloalkyl, phenyl, 1-naphthyl, 2-naphthyl, C$_7$–C$_{14}$-aralkyl, C$_7$–C$_{14}$-aralkyl or a radical

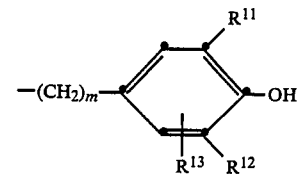

m being 0, 1 or 2, n being 0 or 1, R$^{11}$, R$^{12}$ and R$^{13}$ independently of one another being hydrogen, C$_1$–C$_{20}$-alkyl, cyclohexyl or phenyl and R$^{14}$ being C$_1$–C$_6$-alkyl, phenyl, cyclohexyl, benzyl or tolyl.

11. A composition according to claim 10, in which the lubricant is a mineral oil or a synthetic lubricant.

* * * * *

UNITED STATES PATENT AND TRADEMARK OFFICE
CERTIFICATE OF CORRECTION

PATENT NO. : 4,741,846
DATED : MAY 3, 1988
INVENTOR(S) : SAMUEL EVANS, ET AL.

It is certified that error appears in the above-identified patent and that said Letters Patent is hereby corrected as shown below:

On the cover page, Item [75] after Switzerland, should read -- Hans-Rudolf Meier, Marly, Switzerland --.

Signed and Sealed this

Thirty-first Day of December, 1991

Attest:

HARRY F. MANBECK, JR.

*Attesting Officer*        *Commissioner of Patents and Trademarks*